United States Patent [19]

Broadhurst

[11] 4,132,713
[45] Jan. 2, 1979

[54] PROCESS FOR THE PREPARATION OF N-SUBSTITUTED HALOPYRROLIDONES

[75] Inventor: Michael D. Broadhurst, El Cerrito, Calif.

[73] Assignee: Stauffer Chemical Company, Westport, Conn.

[21] Appl. No.: 864,021

[22] Filed: Dec. 23, 1977

[51] Int. Cl.² .......................................... C07D 207/26
[52] U.S. Cl. .................... 260/326.5 FL; 260/326.5 S; 260/326.5 SF; 71/95
[58] Field of Search ................ 260/326.5 FL, 326.5 S

[56] References Cited

U.S. PATENT DOCUMENTS 3,488,732  1/1970  Heiba et al. ..................... 260/343.6
4,069,038  1/1978  Teach ........................... 260/326.5 FL Primary Examiner—Jose Tovar
Attorney, Agent, or Firm—M. Henry Heines

[57] ABSTRACT

A novel process is disclosed herein for the preparation of N-substituted halopyrrolidones of the formula

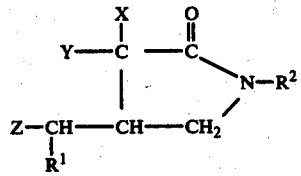

in which X is selected from the group consisting of hydrogen, chlorine, and methyl;
Y is selected from the group consisting of hydrogen, chlorine, and bromine;
Z is selected from the group consisting of chlorine and bromine;
$R^1$ is selected from the group consisting of hydrogen and $C_1$–$C_4$ alkyl; and
$R^2$ is selected from the group consisting of $C_1$–$C_6$ alkyl, $C_3$–$C_6$ alkenyl, $C_1$–$C_6$ haloalkyl, $C_3$–$C_7$ cycloalkyl, $C_4$–$C_8$ cycloalkylalkyl, benzyl, chlorobenzyl, and

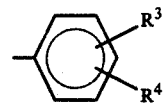

in which $R^3$ is selected from the group consisting og hydrogen, $C_1$–$C_4$ alkyl, acetyl, chlorine, bromine, fluorine, iodine, trifluoromethyl, nitro, cyan, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluoromethylsulfonyl, pentafluoropropionamido, and 3-methylureido; and $R^4$ is selected from the group consisting of hydrogen, $C_1$–$C_4$ alkyl, chlorine, and trifluoromethyl;

which comprises the intramolecular cyclization of an α-halogen-containing N-2-alkenyl amide at a temperature of from about 60° C to about 200° C in the presence of a catalytic amount of a transition-metal-containing catalyst in which the transition metal is selected from the group consisting of vanadium, molybdenum, ruthenium, silver, and copper.

17 Claims, No Drawings

PROCESS FOR THE PREPARATION OF N-SUBSTITUTED HALOPYRROLIDONES

BACKGROUND OF THE INVENTION

Certain N-substituted halopyrrolidones are known to be useful as herbicides of general application. Such compounds and their utility are disclosed in commonly assigned copending applications Ser. No. 647,962, filed Jan. 9, 1976, and Ser. No. 647,963, filed Jan. 9, 1976. These compounds in general have the following formula

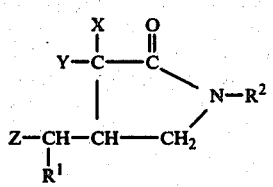

in which
X is selected from the group consisting of hydrogen, chlorine, and methyl;
Y is selected from the group consisting of hydrogen, chlorine, and bromine;
Z is selected from the group consisting of chlorine and bromine;
$R^1$ is selected from the group consisting of hydrogen and $C_1$–$C_4$ alkyl; and
$R^2$ is selected from the group consisting of $C_1$–$C_6$ alkyl, $C_3$–$C_6$ alkenyl, $C_1$–$C_6$ haloalkyl, $C_3$–$C_7$ cycloalkyl, $C_4$–$C_8$ cycloalkylalkyl, benzyl, chlorobenzyl, and

in which $R^3$ is selected from the group consisting of hydrogen, $C_1$–$C_4$ alkyl, acetyl, chlorine, bromine, fluorine, iodine, trifluoromethyl, nitro, cyano, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluoromethylsulfonyl, pentafluoropropionamido, and 3-methylureido; and $R^4$ is selected from the group consisting of hydrogen, $C_1$–$C_4$ alkyl, chlorine, and trifluoromethyl.

According to the above-mentioned references, the compounds are prepared by the intramolecular cyclization of an α-halogen-containing N-2-alkenyl amide in the presence of a catalytic amount of ferrous ion.

It has now been discovered that the intramolecular cyclization referred to above can be catalyzed by catalysts other than ferrous ion. It is therefore an object of the present invention to provide a novel process for the preparation of N-substituted halopyrrolidones of formula (I). Other objects of the invention will be evident from the following description.

BRIEF DESCRIPTION OF THE INVENTION

This invention relates to a process for the preparation of a compound of formula (I) above, which comprises heating an α-halogen-containing N-2-alkenyl amide of the formula

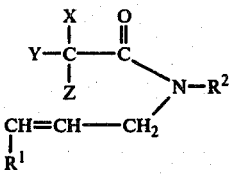

in which X, Y, Z, $R^1$, and $R^2$ are as defined above, to a temperature of from about 60° C. to about 200° C., in the presence of a catalytic amount of a transition-metal-containing catalyst in which the transition metal is selected from the group consisting of vanadium, molybdenum, ruthenium, silver, and copper.

In a preferred embodiment of the process, the halopyrrolidone of Formula (I) and the N-2-alkenyl amide of Formula (II) are defined such that X is chlorine, Y is selected from the group consisting of hydrogen and chlorine, Z is selected from the group consisting of chlorine and bromine, $R^1$ is hydrogen, and $R^2$ is selected from the group consisting of allyl and

in which $R^3$ is selected from the group consisting of $C_1$–$C_4$ alkyl, chlorine, bromine, trifluoromethyl, and cyano, and $R^4$ is selected from the group consisting of hydrogen and $C_1$–$C_4$ alkyl.

Other preferred embodiments are described in the remainder of this specification. All carbon atom ranges stated herein are intended to be inclusive of their upper and lower limits.

DETAILED DESCRIPTION OF THE INVENTION

The α-halogen-containing N-2-alkenyl amide of Formula (II) above which is used as the starting material in the process of the present invention can be prepared by any conventional technique known in the art. One such technique involves the acylation of a primary amine followed by treatment with a 2-alkenyl halide, both reagents appropriately substituted to give the desired final product, and both reactions occurring in the presence of a base:

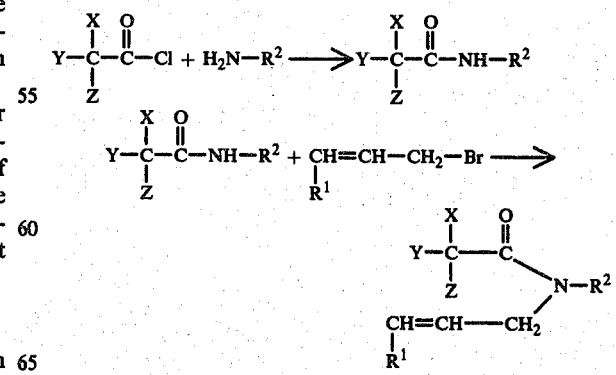

Alternatively, the reaction sequence can be conducted in reverse to yield the same product:

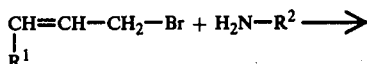

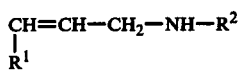

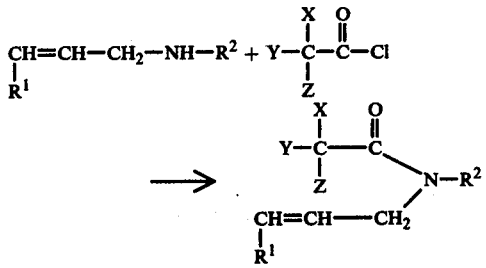

Primary amines capable of use in the above preparation are, in most cases, commercially available, but can be prepared in any event by methods well documented in the chemical literature. Such documentation can be found in Wagner and Zook, "Synthetic Organic Chemistry," John Wiley and Sons, New York (1961), Chapter 24.

The cyclization of the resulting α-halogen-containing N-2-alkenyl amide is conducted in the presence of a catalyst containing one or more of the metals vanadium, molybdenum, ruthenium, silver, and copper, at a temperature ranging from about 60° C. to about 200° C. The preferred temperature range is from about 80° C. to about 150° C. Since the reaction occurs entirely in the liquid phase, the process does not have a critical operating pressure, but is operable over a wide pressure range, subject only to considerations of economy and materials of construction. It is most convenient, however, to conduct the reaction at approximately atmospheric pressure.

The term "transition-metal-containing catalyst" is used herein to designate a catalyst consisting of one or more of the five metals mentioned above chemically bound with other elements in the form of metal-containing compounds. Examples of such compounds are the alkylated metal, the phenylated metal, and salts and oxides of the metal.

The metal-containing compounds can also be present in the form of complexes with common complexing agents, examples of which are triphenylphosphine, carbon monoxide, and tertiary amines. Examples of tertiary amines which are useful in the present invention are pyridine, 2,2'-dipyridyl, 2,2'-dipyridylamine, and tetramethylenediamine. When the transition metal is copper, the catalytic activity of the compound is frequently enhanced by the addition of such an amine. The best results are generally achieved when the relative quantities of amine and copper compound are selected such that the ratio of copper atoms to nitrogen atoms, excluding the nitrogen atoms in the amide to be cyclized, is between about 1:1 and about 1:4.

The catalyst can either be present as an undissolved solid in the reaction mixture, or as a solute in solution with the starting amide or solvent, when a solvent is used. In general, it is preferred that the catalyst be dissolved. When an insoluble transition metal catalyst is used, solubilization can frequently be achieved by selection of the proper type and quantity of complexing agent, such as those listed above. Solubilization can also be achieved by raising the system temperature.

Whether the catalyst is undissolved or in solution, the reaction will proceed without agitation. When agitation is used, however, the progress of the reaction will be significantly enhanced. Agitation is particularly advantageous when the catalyst is not dissolved in the mixture, since agitation in such case will increase the contact between the catalyst and the starting amide. Agitation can be achieved by any conventional means, for example: stirring, inert gas purging, the use of baffles in the reaction vessel, or conducting the reaction at reflux.

It will be apparent to one skilled in the art that the quantity of transition-metal-containing catalyst which will constitute a "catalytic amount" will be any quantity that serves to increase the rate of reaction, and that larger quantities will provide a greater increase. The quantity used in any particular application will be determined in large part by the individual needs of the manufacturing facility. Factors which enter into such a determination include the catalyst cost, recovery costs, desired reaction time, and system capacity. Aside from these considerations, the catalyst quantity is not a critical feature of the invention, and can vary over a wide range. It will be most convenient to use an amount of catalyst which comprises from about 0.5 mole % to about 20.0 mole %, preferably from about 1.0 mole % to about 10.0 mole %, based on the initial quantity of N-2-alkenyl amide.

Although the reaction can be conducted without the use of a solvent, a variety of solvents can be used to facilitate the handling of the system components, to aid in solubilization of the catalyst, to facilitate agitation, and to improve reaction control by minimizing decompositions and by-product formation and by controlling reaction rate. Any inert solvent can be used, including, but not limited to, the following:

aliphatic compounds, for example heptane or octane;
aromatic compounds, for example toluene, xylene, or mesitylene;
chlorinated aliphatic or aromatic compounds, for example, 1,2-dichloroethane or chlorobenzene;
ethers, for example 1,2-dimethoxyethane, diethyl ether, tetrahydrofuran, or 1,4-dioxane;
alcohols, for example isopropanol or ethylene glycol; and
carboxylic acids, for example acetic, propionic, or butyric acid.

The pyrrolidone produced by the reaction can be recovered from the reaction mixture by any conventional technique. Examples of such techniques are solvent extraction, crystallization, sublimation and distillation.

The herbicide utility of the halopyrrolidones produced by the present invention is fully demonstrated and described in the two copending applications referred to above. The descriptions in these applications are incorporated herein by reference.

The following examples are offered to illustrate the practice of the present invention and are not intended to limit the invention in any manner.

EXAMPLES 1–6

These examples, as illustrated in Table I, demonstrate the preparation of 3-chloro-4-chloromethyl-1-(m-trifluoromethylphenyl)-2-pyrrolidone using a variety of silver-, ruthenium-, molybdenum-, and vanadium-containing catalysts. In each case, 10.0 grams of N- Allyl -3'-trifluoromethyl-2,2-dichloroacetanilide was used as the starting material. No solvent was used. The catalyst and its mole percent based on the acetanilide are indicated in the table for each example. As also indicated in the table, pyridine was added to the reaction mixture in some cases. The reaction occurred in a flask equipped with a magnetic stirrer. The reaction mixture was sampled at intervals and analyzed by gas-liquid chromatography to monitor the reaction progress. The results of the last analysis in each case are listed. Product recovery was then achieved by dissolution of the reaction mixture in toluene, followed by washing of the toluene solution with dilute aqueous acid to remove the catalyst, and finally distillation to remove the solvent. The molecular structure of the product pyrrolidone was confirmed by nuclear magnetic resonance (NMR), mass spectrometry (MS), and infrared (IR) analyses.

TABLE I

Preparation of 3-Chloro-4-chloromethyl-1-(metrifluoromethylphenyl)-2-pyrrolidone

| Ex. | Catalyst[a] | Temperature (°C) | Time (hours) | Yield (%) |
|---|---|---|---|---|
| 1 | Ag$_2$O (10) | 150 | 5 | 5 |
| 2 | Ag$_2$O (10) with pyridine (40) | 150 | 6 | 1 |
| 3 | RuO$_2$ (3) with pyridine (20) | 145 | 3 | 12 |
| 4 | RuCl$_2$ [P(C$_6$H$_5$)$_3$]$_3$ (2) | 125 | 17 | 64 |
| 5 | [Mo(CO)$_3$(Cp)$_2$]$_2$[b] (1) | 100 | 8 | 13 |
| 6 | VCl$_3$ (10) | 150 | 10 | 4 |

[a]Mole percent based on starting acetanilide is shown in parentheses.
[b]Cp : cyclopentadienyl

EXAMPLES 7-13

The product made in Examples 1-6 was prepared in Examples 7-13 using copper-containing catalysts. The procedure was otherwise the same as that followed in Examples 1-6. The results are listed in Table II.

TABLE II

Further Preparation of 3-Chloro-4-chloromethyl-1-(metripluoromethylphenyl)-2-pyrrolidone

| Example | Catalyst[a] | Temperature (°C) | Time (hours) | Yield (%) |
|---|---|---|---|---|
| 7 | Cu$_2$Cl$_2$ (5) | 150 | 8 | 27 |
| 8 | Cu$_2$Cl$_2$ (5) with 2,2'-dipyridyl (10) | 125 | 2.5 | 59 |
| 9 | Cu$_2$O (10) | 145 | 11 | 26 |
| 10 | Cu$_2$O (10) with 2,2'-dipyridyl (10) | 100 | 4 | 64 |
| 11 | Cu$_2$O (10) with pyridine (20) | 100 | 1.5 | 65 |
| 12 | Cu$_2$O (10) with TMEDA[b](10) | 100 | 9 | 30 |
| 13 | Cu$_2$O (10) with 2,2'-dipyridylamine (20) | 100 | 3 | 26 |

[a]Mole percent based on starting acetanilide shown in parentheses.
[b]TMEDA : tetramethyethylenediamine

EXAMPLE 14

This example illustrates the use of a solvent in a large scale preparation of the product prepared in Examples 1-13. A 2000 milliliter flask equipped with overhead stirrer and reflux condenser under nitrogen was charged with 280 grams (0.88 mole at 98% purity) of the starting acetanilide, 6.293 grams (44.0 millimoles, 5 mole % based on the acetanilide) of Cu$_2$O, 27.8 grams (0.354 moles, 40 mole % based on the acetanilide) of pyridine, and 200 milliliters of toluene. The mixture was heated to reflux for approximately one hour. Analysis by gas-liquid chromatography of the reaction mixture, exclusive of the solvent and catalyst, yielded 0.25% starting material, 97.62% product, and 2.13% impurities. Product recovery was achieved by washing with water and concentrated HCl, followed by toluene and aqueous NaCl washes, drying over Na$_2$SO$_4$, and evaporation under vacuum. The structure of the product was confirmed by NMR, MS, and IR analyses.

The following examples illustrate the utility of the process of the invention in preparing compounds other than that prepared in Examples 1-14.

EXAMPLE 15

3-Chloro-4-chloromethyl-1-(2,6-diethylphenyl)-2-pyrrolidone

A 50-milliliter flask equipped with magnetic stirrer and reflux condenser was charged with the following:

| | |
|---|---|
| 4.0 grams (13 millimoles) | N-allyl-N-(2,6-diethylphenyl)-2,2-dichloroacetamide |
| 0.38 grams (2.7 millimoles) | Cu$_2$O |
| 0.8 milliliters (10 millimoles) | pyridine |
| 10 milliliters | toluene |

The reaction mixture was heated at reflux (128° C.) for 13 hours. The product mixture was then poured into water, acidified to pH 1 with concentrated HCl, extracted with xylene, washed with water, and stripped of solvent to yield 2.4 grams of a heavy dark oil, representing a 60% yield of the title compound, structure confirmed by NMR.

EXAMPLE 16

4-Chloromethyl-3,3-dichloro-1-(m-trifluoromethylphenyl)-2-pyrrolidone

A 100 milliliter flask with Claisen head, condenser, and magnetic stirrer was charged with the following:

| | |
|---|---|
| 13.0 grams (37.5 millimoles) | N-allyl-N-(m-trifluoromethylphenyl)-2,2,2-trichloroacetamide |
| 0.54 grams (3.8 millimoles) | Cu$_2$O |
| 1.2 milliliters (15 millimoles) | pyridine |
| 40 milliliters | toluene |

The reaction mixture was heated at reflux (109° C.) for 115 minutes. The mixture was then poured into water, acidified to pH 1 with concentrated HCl, extracted with a 2:1 ether-toluene mixture, washed with 1N HCl and water, and stripped of the solvent. The result was 9.5 grams of a dark solid with melting point 87-100° C., representing 73% yield of the title compound, structure confirmed by NMR.

EXAMPLE 17

1-Allyl-3-chloro-4-chloromethyl-2-pyrrolidone

A 100 milliliter flask equipped with magnetic stirrer and reflux condenser was charged with the following:

| | |
|---|---|
| 25.0 grams (97%, 0.117 moles) | N,N-diallyl-2,2-dichloroacetamide |
| 1.71 grams (12 millimoles) | Cu$_2$O |
| 3.8 milliliters (47 millimoles) | pyridine |

-continued

| | |
|---|---|
| 25 milliliters | toluene |

The reaction mixture was heated at reflux (117° C.) for 2 hours. The mixture was then poured into water and acidified to pH 1 with concentrated HCl. The organic phase was washed with 5% HCl and water, and the organics were stripped to yield 16.8 grams of a dark oil, representing 69% yield of the title compound. The purity was determined to be 57% by weight, according to gas-liquid chromatographic comparison with a sample of the title compound of known purity.

EXAMPLE 18

3-Bromo-4-bromomethyl-1-(3-chlorophenyl)-2-pyrrolidone

A 50 milliliter flask equipped with magnetic stirrer and reflux condenser was charged with the following:

| | |
|---|---|
| 2.0 grams (87%, 4.8 millimoles) | N-allyl-N-(3-chlorophenyl)-2,2-dibromoacetamide |
| 0.039 grams (0.3 millimoles) | $Cu_2O$ |
| 0.172 grams (2.2 millimoles) | pyridine |
| 10 millimeters | toluene |

The reaction mixture was heated at reflux (112° C.) for 12 hours. The mixture was then dissolved in methylene dichloride, then washed with 5% HCl and water. The solvent was then evaporated to yield 0.4 grams of a dark oil, representing 23% yield of the title compound, structure confirmed by gas chromatography and MS.

What is claimed is:

1. A process for the preparation of a compound having the formula $$Y-\underset{\underset{Z-CH-CH-CH_2}{|}}{\overset{\overset{X}{|}}{C}}-\overset{\overset{O}{\|}}{C}-N-R^2$$
$$\underset{R^1}{|}$$

in which

X is selected from the group consisting of hydrogen, chlorine, and methyl;

Y is selected from the group consisting of hydrogen, chlorine, and bromine;

Z is selected from the group consisting of chlorine and bromine;

$R^1$ is selected from the group consisting of hydrogen and $C_1$–$C_4$ alkyl; and $R^2$ is selected from the group consisting of $C_1$–$C_6$ alkyl, $C_3$–$C_6$ alkenyl, $C_1$–$C_6$ haloalkyl, $C_3$–$C_7$ cycloalkyl, $C_4$–$C_8$ cycloalkylalkyl, benzyl, chlorobenzyl, and

[phenyl ring with $R^3$, $R^4$ substituents]

in which $R^3$ is selected from the group consisting of hydrogen, $C_1$–$C_4$ alkyl, acetyl, chlorine, bromine, fluorine, iodine, trifluoromethyl, nitro, cyano, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluromethylsulfonyl, pentafluoropropionamido, and 3-methylureiodo; and $R^4$ is selected from the group consisting of hydrogen, $C_1$–$C_4$ alkyl, chlorine, and trifluoromethyl;

which comprises heating an α-halogen-containing N-2-alkenyl amide of the formula $$Y-\underset{\underset{CH=CH-CH_2}{|}}{\overset{\overset{X}{|}}{C}}-\overset{\overset{O}{\|}}{C}\diagdown N-R^2$$
$$\underset{R^1}{|}$$

in which X, Y, Z, $R^1$, and $R^2$ are as defined above, to a temperature of from about 60° C. to about 200° C., in the presence of a catalytic amount of a transition-metal-containing catalyst in which the transition metal is selected from the group consisting of vanadium, molybdenum, ruthenium, silver, and copper.

2. A process according to claim 1 in which X is chlorine; Y is selected from the group consisting of hydrogen and chlorine; Z is selected from the group consisting of chlorine and bromine; $R^1$ is hydrogen; and $R^2$ is selected from the group consisting of allyl and

[phenyl ring with $R^3$, $R^4$ substituents]

in which $R^3$ is selected from the group consisting of $C_1$–$C_4$ alkyl, chlorine, bromine, trifluoromethyl, and cyano; and $R^4$ is selected from the group consisting of hydrogen and $C_1$–$C_4$ alkyl.

3. A process according to claim 1 in which the N-2-alkenyl amide is heated to a temperature of from about 80° C. to about 150° C.

4. A process according to claim 1 in which the transition-metal-containing catalyst is present in an amount ranging from about 0.5 mole % to about 20.0 mole %, based on the initial quantity of N-2-alkenyl amide.

5. A process according to claim 1 in which the transition-metal-containing catalyst is present in an amount ranging from about 1.0 mole % to about 10.0 mole %, based on the initial quantity of N-2-alkenyl amide.

6. A process according to claim 1 in which the transition-metal-containing catalyst is selected from the group consisting of vanadium trichloride, cyclopentadienylmolybdenum tricarbonyl dimer, ruthenium dioxide, tris-triphenylphosphine ruthenium dichloride, silver oxide, cuprous chloride, and cuprous oxide.

7. A process according to claim 1 in which the transition-metal-containing catalyst is selected from the group consisting of tris-triphenylphosphine ruthenium dichloride, cuprous chloride, and cuprous oxide.

8. A process according to claim 1 in which the transition-metal-containing catalyst is selected from the group consisting of cuprous chloride and cuprous oxide, said process being conducted in the further presence of a tertiary amine in such quantity that the ratio of copper atoms to nitrogen atoms, excluding the nitrogen atoms in the N-2-alkenyl amide, is between about 1:1 and about 1:4.

9. A process according to claim 8 in which the tertiary amine is selected from the group consisting of pyridine, 2,2'-dipyridyl, 2,2'-dipyridylamine, and tetramethylethylenediamine.

10. A process according to claim 1 in which X is chlorine, Y is hydrogen, Z is chlorine, $R^1$ is hydrogen, and $R^2$ is 3-trifluoromethylphenyl; and the transition-metal-containing catalyst is tris-triphenylphosphine ruthenium dichloride.

11. A process according to claim 1 in which X is chlorine, Y is hydrogen, Z is chlorine, $R^1$ is hydrogen, and $R^2$ is 3-trifluoromethylphenyl; and the transition-metal-containing catalyst is cuprous chloride.

12. A process according to claim 11 which is conducted in the further presence of 2,2'-dipyridyl in a mole ratio of from about 1:1 to about 4:1 with respect to the cuprous chloride.

13. A process according to claim 1 in which X is chlorine, Y is hydrogen, Z is chlorine, $R^1$ is hydrogen, and $R^2$ is 3-trifluoromethylphenyl; and the transition-metal-containing catalyst is cuprous oxide.

14. A process according to claim 13 which is conducted in the further presence of 2,2'-dipyridyl in a mole ratio of from about 1:1 to about 4:1 with respect to the cuprous oxide.

15. A process according to claim 13 which is conducted in the further presence of tetramethylethylenediamine in a mole ratio of from about 1:1 to about 4:1 with respect to the cuprous oxide.

16. A process according to claim 13 which is conducted in the further presence of 2,2'-dipyridylamine in a mole ratio of from about 2:3 to about 8:3 with respect to the cuprous oxide.

17. A process according to claim 13 which is conducted in the further presence of pyridine in a mole ratio of from about 2:1 to about 8:1 with respect to the cuprous oxide.

* * * * *